US009611285B2

(12) United States Patent
Parkot et al.

(10) Patent No.: US 9,611,285 B2
(45) Date of Patent: Apr. 4, 2017

(54) FUCOSYLTRANSFERASES AND THEIR APPLICATIONS

(71) Applicant: Jennewein Biotechnologie GmbH, Rheinbreitbach (DE)

(72) Inventors: Julia Parkot, Cologne (DE); Eric Huefner, Hennef (DE); Stefan Jennewein, Aachen (DE); Lothar Elling, Aachen (DE); Leonie Engels, Aachen (DE)

(73) Assignee: Jennewein Biotechnologie GmbH, Rheinbreitbach (DE)

( * ) Notice: Subject to any disclaimer, the term of this patent is extended or adjusted under 35 U.S.C. 154(b) by 0 days.

(21) Appl. No.: 13/946,845

(22) Filed: Jul. 19, 2013

(65) Prior Publication Data

US 2014/0024820 A1 Jan. 23, 2014

Related U.S. Application Data

(63) Continuation of application No. PCT/EP2011/074291, filed on Dec. 30, 2011.

(30) Foreign Application Priority Data

Jan. 20, 2011 (EP) .................... 11151571

(51) Int. Cl.
*C12P 19/18* (2006.01)
*C07H 3/04* (2006.01)
(Continued)

(52) U.S. Cl.
CPC ............. *C07H 3/04* (2013.01); *C12N 9/1051* (2013.01); *C12P 19/18* (2013.01); *C12P 21/005* (2013.01)

(58) Field of Classification Search
None
See application file for complete search history.

(56) References Cited

U.S. PATENT DOCUMENTS 5,807,732 A * 9/1998 Lowe et al. .................. 435/358
2002/0037570 A1* 3/2002 Taylor et al. ................ 435/193
(Continued)

FOREIGN PATENT DOCUMENTS

EP  1 243 647 A1  9/2002
EP  1 275 714 A1  1/2003
(Continued)

OTHER PUBLICATIONS

Drouillard et al., "Large-scale synthesis of H-antigen oligosaccharides by expressing Helicobacter pylori alpha-1,2-fucosyltransferase in metabolically engineered *Escherichia coli* cells", Angewandte Chemie, International Edition, vol. 45, pp. 1778-1780, 2006.*

(Continued)

*Primary Examiner* — Robert Mondesi
*Assistant Examiner* — Richard Ekstrom
(74) *Attorney, Agent, or Firm* — Klarquist Sparkman, LLP

(57) ABSTRACT

The present invention relates to nucleic acid and amino acid sequences from *Escherichia coli* serogroup O126, coding for/representing a novel alpha-1,2-fucosyltransferase. The invention also provides uses and methods for using the alpha-1,2-fucosyltransferase to generate fucosylated products, such as oligosaccharides, (glyco)proteins, or (glyco)lipids, in particular oligosaccharides found in human milk, such as 2'-fucosyllactose.

16 Claims, 11 Drawing Sheets

(51) Int. Cl.
C12N 9/10 (2006.01)
C12P 21/00 (2006.01)

(56) References Cited

U.S. PATENT DOCUMENTS

2002/0127655 A1* 9/2002 Holmes et al. ............. 435/69.7
2014/0031541 A1* 1/2014 Heidtman et al. ......... 536/123.1

FOREIGN PATENT DOCUMENTS

WO     WO 00/26383     5/2000
WO     WO 2010070104 A1 *   6/2010

OTHER PUBLICATIONS

Li et al., "Characterization of a novel alpha-1,2-fucosyltransferase of Escherichia coli O128:B12 and functional investigation of its common motif", Biochemistry, vol. 47, pp. 378-387, 2008.*

Database UniProt Accession No. A6M9C2 "Glycosyltransferase," (Jul. 24, 2007).
Albermann et al., "Synthesis of the milk oligosaccharide 2'-fucosyllactose using recombinant bacterial enzymes," Carbohydrate Research 334(2): 97-103 (Aug. 23, 2001).
Barratt et al., "Multiple, distinct isoforms of sucrose synthase in Pea," Plant Physiology 127(2):655-664 (Oct. 2001).
International Preliminary Report on Patentability and amended pages submitted in response to the Written Opinion from parent PCT Application No. PCT/EP2011/074291 (mailed Mar. 26, 2013).
International Search Report and Written Opinion from parent PCT Application No. PCT/EP2011/074291 (mailed Feb. 22, 2012).
Liu et al, "Sequencing and analysis of the Escherichia coli serogroup O117, O126, and O146 o-antigen gene clusters and development of PCR assays targeting DNA sequences," Molecular and Cellular Probes 21(4):295-302 (May 11, 2007).
Fratamico et al., "Sequence of the Escherichia coli O121 O-Antigen Gene Cluster and Detection of Enterohemorrhagic E. coli O121 by PCR Amplification of the wzx and wzy Genes," Journal of Clinical Microbiology 41(7):3379-3383 (Jul. 2013).

* cited by examiner

Sequence of gene coding for alpha-1,2-fucosyltransferase WbgL from *E. oli* O126
(SEQ ID NO: 1)

ATGAGCATTATTCGTCTGCAGGGTGGTCTGGGTAATCAGCTGTTTCAGTTTAGCTT
TGGTTATGCCCTGAGCAAAATTAATGGTACACCGCTGTATTTCGACATTAGCCATT
ATGCCGAAAACGATGATCATGGTGGTTATCGTCTGAATAATCTGCAGATTCCGGA
AGAATATCTGCAGTATTATACCCCGAAAATTAATAATATTTATAAACTGCTGGTG
CGTGGCAGCCGTCTGTATCCGGATATTTTTCTGTTTCTGGGCTTTTGCAACGAATT
TCATGCCTATGGCTACGATTTTGAATATATTGCCCAGAAATGGAAAAGCAAAAAA
TACATTGGCTACTGGCAGAGCGAACACTTTTTTCATAAACATATTCTGGACCTGA
AAGAATTTTTTATTCCGAAAAATGTGAGCGAACAGGCAAATCTGCTGGCAGCAAA
AATTCTGGAAAGCCAGAGCAGCCTGAGCATTCATATTCGTCGTGGCGATTATATT
AAAAACAAAACCGCAACCCTGACACATGGTGTTTGTAGCCTGGAATATTATAAAA
AAGCCCTGAACAAAATCCGCGATCTGGCAATGATTCGTGATGTGTTTATCTTTAG
CGACGATATCTTCTGGTGCAAAGAAAATATTGAAACCCTGCTGAGCAAAAAATAT
AATATTTATTATAGCGAAGATCTGAGCCAAGAAGAGGATCTGTGGCTGATGAGCC
TGGCAAATCATCATATTATTGCCAATAGCAGCTTTAGTTGGTGGGGTGCATATCT
GGGTAGCAGCGCAAGCCAGATTGTTATTTATCCGACCCCGTGGTATGATATTACC
CCGAAAAACACCTATATCCCGATTGTGAACCATTGGATCAACGTTGATAAACATA
GCAGCTGCTAA

Sequence of polypeptide/protein WbgL (SEQ ID NO: 2)

MSIIRLQGGLGNQLFQFSFGYALSKINGTPLYFDISHYAENDDHGGYRLNNLQIPEEYL
QYYTPKINNIYKLLVRGSRLYPDIFLFLGFCNEFHAYGYDFEYIAQKWKSKKYIGYW
QSEHFFHKHILDLKEFFIPKNVSEQANLLAAKILESQSSLSIHIRRGDYIKNKTATLTHG
VCSLEYYKKALNKIRDLAMIRDVFIFSDDIFWCKENIETLLSKKYNIYYSEDLSQEEDL
WLMSLANHHIIANSSFSWWGAYLGSSASQIVIYPTPWYDITPKNTYIPIVNHWINVDK
HSSC

Fig. 1A

1: *E. coli* JM109(DE3) pET22bHIS6PropepwbgL, insoluble fraction
2: *E. coli* JM109(DE3) pET22bHIS6PropepwbgL, crude extract
3 + 5: wash fractions
4: Protein standard PageRuler, Fermentas
5: purified His$_6$-Propeptide-WbgL 1: *E. coli* JM109(DE3) pET22bHIS6PropepwbgL, crude extract
2: Protein standard
3 + 4: IMAC-Pool
5: *E. coli* JM109(DE3) pET22bHIS6PropepwbgL, insoluble fraction

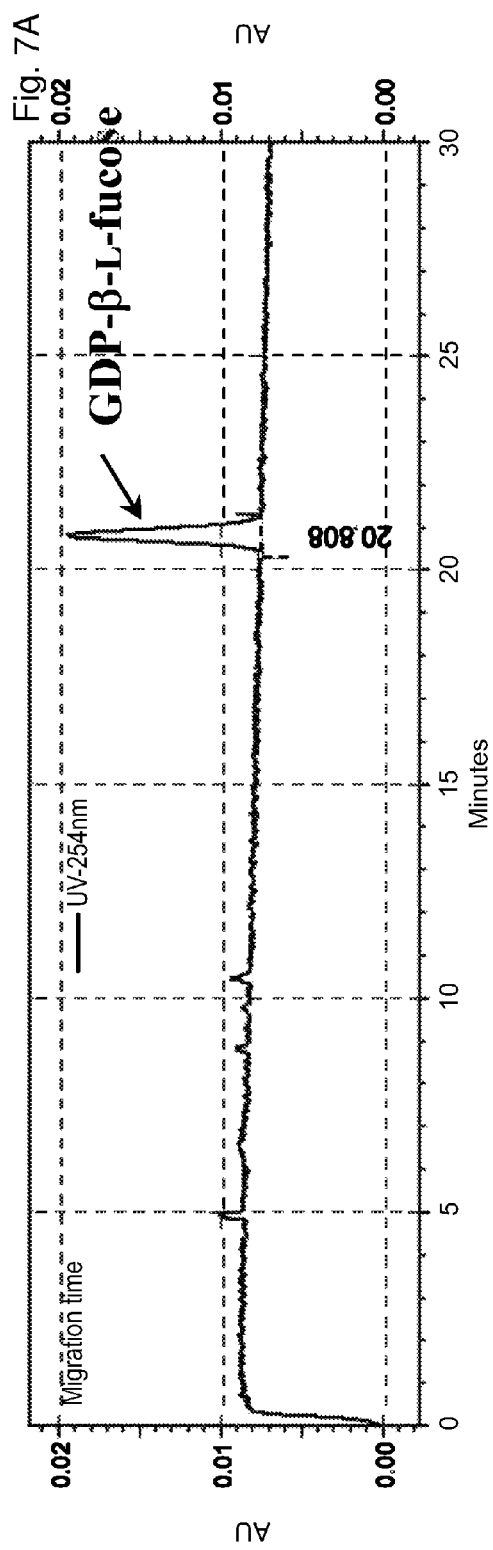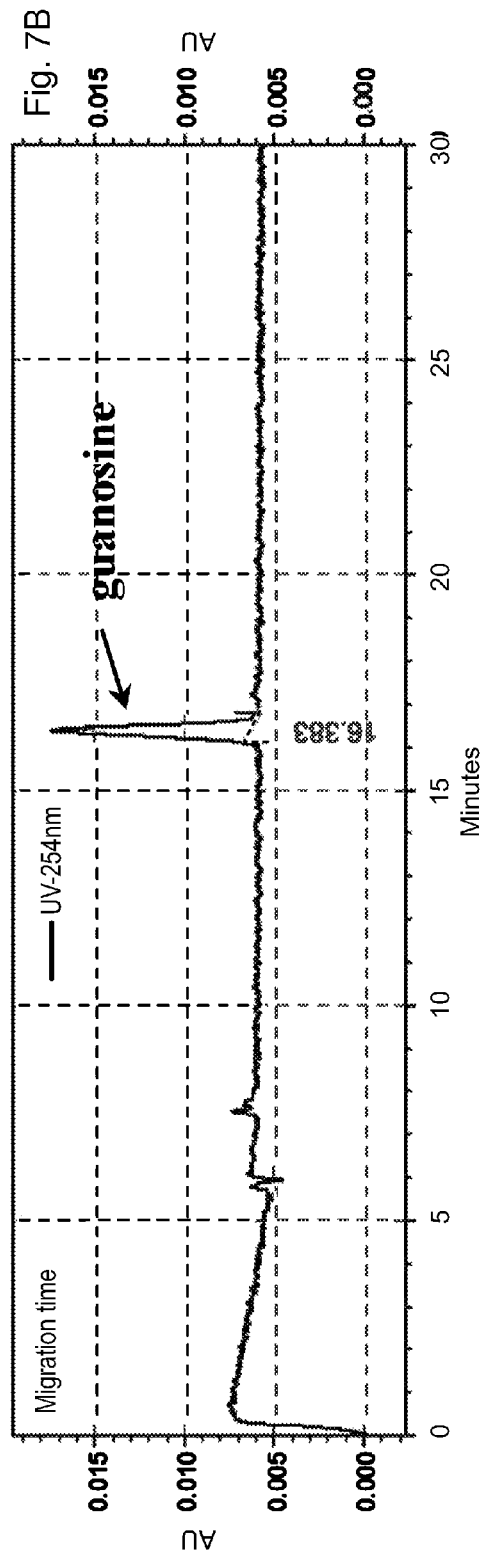

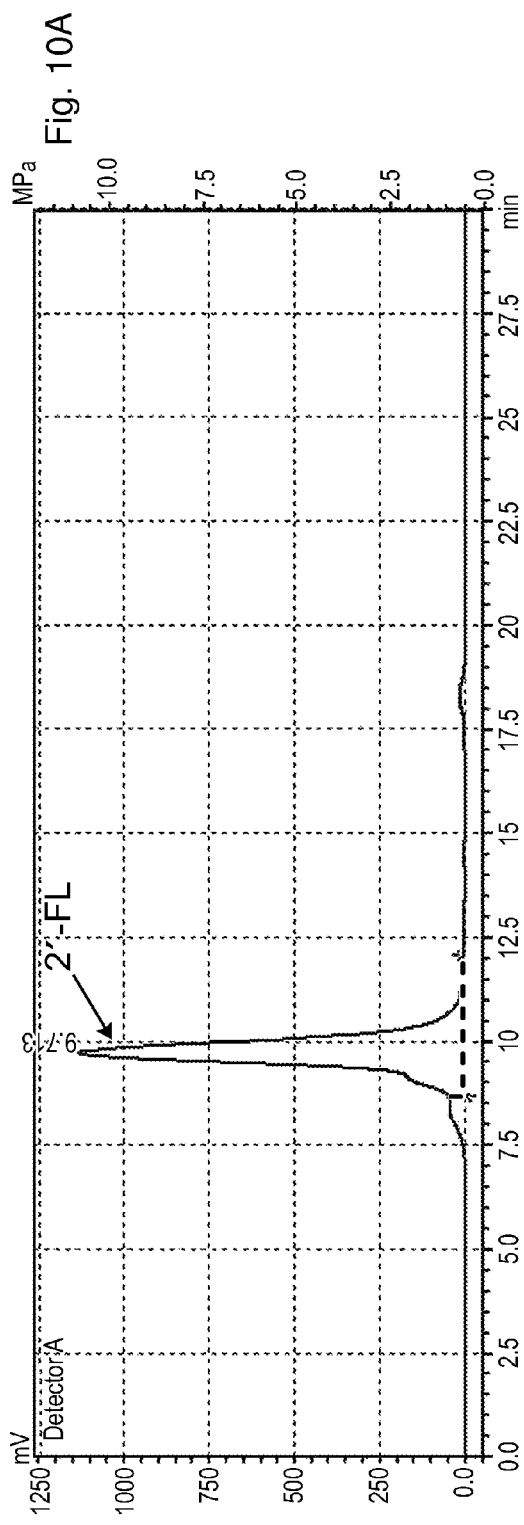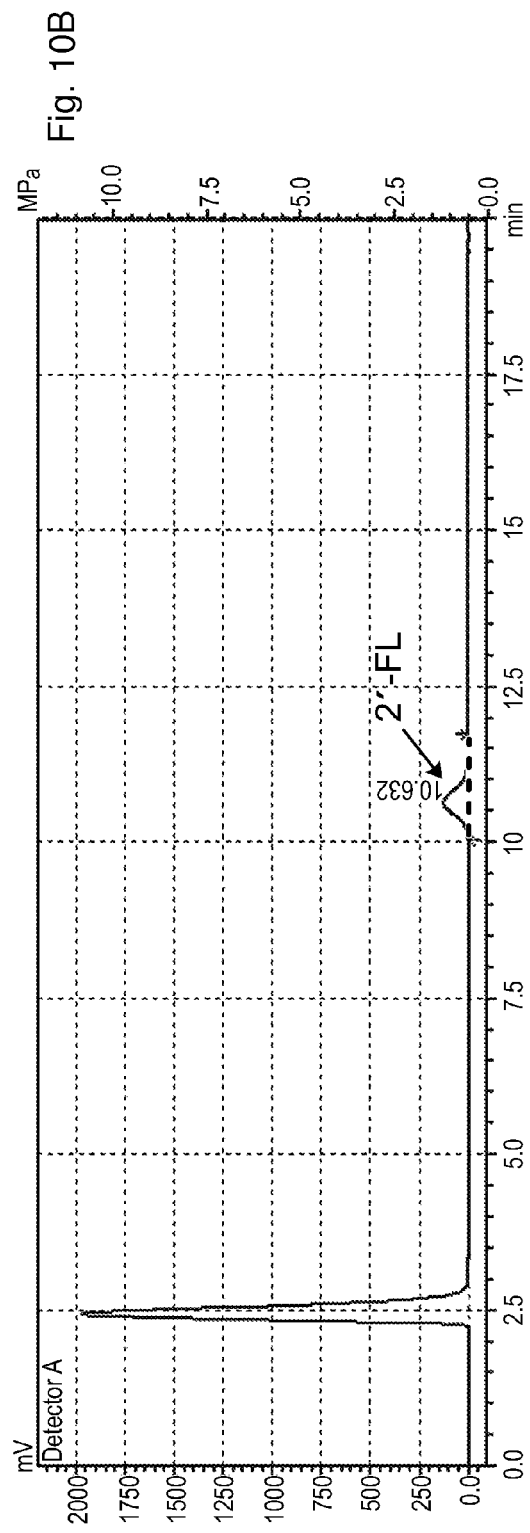

FUCOSYLTRANSFERASES AND THEIR APPLICATIONS

CROSS REFERENCES TO RELATED APPLICATIONS

This application is a continuation of international patent application PCT/EP2011/074291, filed on Dec. 30, 2011 designating the U.S., which international patent application has was published in English and claims priority to European patent application EP 11 151 571.4, filed on Jan. 20, 2011. The entire contents of these priority applications are incorporated herein by reference.

BACKGROUND OF THE INVENTION

The present invention relates to a novel fucosyltransferase and its applications.

Many (glyco)proteins, (glyco)lipids or oligosaccharides require the presence of particular fucosylated structures, in order to exhibit a particular biological activity. E.g., many intercellular recognition mechanisms require a fucosylated oligosaccharide: e.g., in order to be bound by cell adhesion molecules, such as L-selectin, specific cell structures have to comprise fucosylated carbohydrates. Another example for fucosylated structures having a biological function are structures that form the AB0 blood group system. Furthermore, therapeutic (glyco)proteins represent the fastest growing class of pharmaceutical reagents, whereby their pharmacokinetic properties and stability are/is ascribed to their glycans.

Due to their complex nature and inherent chemical properties, the chemical synthesis of glycoconjugates is a major challenge and associated with substantial difficulties. Unlike proteins and nucleic acids, for which automated synthesizers are commercially available, glycans—and let alone glycoconjugates—cannot (yet) be synthesized using a general commercial system. Apart from the requirement to control stereochemistry, the formation of specific linkages remains difficult.

In view of the complexness associated with the chemical or the combined enzymatic/chemical synthesis of glycoconjugates, recent approaches have used glycosyltransferases to enzymatically synthesize (glyco)proteins and (glyco)lipids comprising oligosaccharide residues.

Fucosyltransferases, which belong to enzyme family of glycosyltransferases, are widely expressed in vertebrates, invertebrates, plants and bacteria. They catalyze the transfer of a fucose residue from a donor, generally guanosine-diphosphate fucose (GDP-fucose) to an acceptor, which include oligosaccharides, (glyco)proteins and (glyco)lipids. The thus fucosylated acceptor substrates are involved in a variety of biological and pathological processes.

Based on the site of fucose addition, fucosyltransferases are classified into alpha-1,2-, alpha-1,3/4- and O-fucosyltransferases. Several alpha-1,2-fucosyltransferases have been identified, e.g. in the bacteria *Helicobacter pylori* and *Escherichia coli*, in mammals, *Caenorhabditis elegans* and *Schistosoma mansoni*, as well as in plants. Most of these enzymes can either not be expressed in an active form in bacterial systems, or cannot use lactose as an acceptor.

In mammals, GDP-Fucose is synthesized in the cytoplasm through de novo synthesis and salvage pathway. With the de novo synthesis, GDP-mannose is converted to GDP-fucose via two enzymes, whilst the salvage pathway utilizes the free cytosolic fucose as substrate. In the cell, GDP-fucose becomes concentrated in vesicles and is recognized by fucosyltransferases as a donor substrate. However, the heterologous functional expression of eukaryotic glycosyltransferases, and in particular fucosyltransferases proved difficult in prokaryotic expression systems. Mammalian and in particular human oligosaccharides such as HMOs are not known from prokaryotic sources, thus making the discovery of glycosyltransferases making these oligosaccharides extremely unlikely.

Since the biological activity of many commercially important oligosaccharides, (glyco)proteins and (glyco)lipids depends upon the presence of particular fucose residues, there is a need in the state of the art to efficiently synthesize or produce glycoconjugates that have the desired oligosaccharide residue(s).

SUMMARY OF THE INVENTION

Thus, it is an object of the present invention to provide for tools and methods by means of which fucosylated substrates can be produced in an efficient, time- and cost saving way, which yields high amounts of the desired substrate.

According to the invention, this object is solved, inter alia, by the provision of a polynucleotide, which can be, e.g., isolated, recombinant or synthetic, encoding a polypeptide with alpha-1,2-fucosyltransferase activity and comprising a sequence or consisting of a sequence selected from the group consisting of:
 a) SEQ ID No. 1 of the attached sequence listing;
 b) a nucleic acid sequence complementary to SEQ ID No. 1;
 c) nucleic acid sequences which hybridize under stringent conditions to the nucleic acid sequences defined in a) and b) or their complementary strands.

SEQUENCE LISTING

The Sequence Listing is submitted as an ASCII text file 7291-90210-01_Sequence_Listing.txt, Jul. 19, 2013, 7.85 KB], which is incorporated by reference herein.

The polynucleotide according to the invention (see SEQ ID No. 1) represents a fucosyltransferase of the species *Escherichia coli* serogroup O126.

The newly identified fucosyltransferase has surprising effects since by using them reactions can be performed which are not naturally occurring in the source organism: Within the scope of the present invention it has been found that the above identified alpha-1,2-fucosyltransferase is able to use lactose as substrate and is able to produce fucosylated oligosaccharides, in particular 2'-fucosyllactose. Up to date, none of the known alpha-1,2-fucosyltransferases isolated from bacteria has been shown to use lactose as a natural substrate for the production of fucosyllactose. Thus, the suitability of the newly identified fucosyltransferase to be used for producing fucosylated oligosaccharides is highly surprising, and, thus, its use represents an excellent tool to easily, efficiently and cost-saving produce, e.g., human milk oligosaccharides (HMOs), such as fucosyllactose. Today, more than 80 compounds, belonging to HMOs, have been structurally characterized; they represent a class of complex oligosaccharides that function as prebiotics. Additionally, the structural homology of HMO to epithelial epitopes accounts for protective properties against bacterial pathogens. Within the infants gastrointestinal tract, HMOs selectively nourish the growth of selected bacteria strains and are, thus, priming the development of a unique gut microbiota in breast milk-fed infants.

Since until now, the structural complexity of these oligosaccharides has hindered their synthetic production, the main source for HMOs is still human milk. Thus, there is a need for readily and easily obtainable HMOs, which can be provided by using the—surprisingly suitable—fucosyltransferase presented herein.

According to the present invention, the term "polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. Also, "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Similarly, a "synthetic" sequence, as the term is used herein, means any sequence that has been generated synthetically and not directly isolated from a natural source. "Recombinant" means genetically engineered DNA prepared by transplanting or splicing genes from one species into the cells of a host organism of a different species. Such DNA becomes part of the host's genetic makeup and is replicated.

The term "polynucleotide encoding a polypeptide" as used herein encompasses polynucleotides that include the sequence encoding the polypeptide of the invention, particularly an alpha-1,2-fucosyltransferase having the amino acid sequence as set forth in SEQ ID No. 2. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Variant(s)" as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

The terms "alpha-1,2-fucosyltranferase" or "fucosyltransferase" or a nucleic acid/polynucleotide encoding an "alpha- 1,2-fucosyltranferase" or "fucosyltransferase" refer to a glycosyltransferase that catalyzes the transfer of fucose from a donor substrate, for example, GDP-fucose, to an acceptor molecule in an alpha-1,2-linkage. The acceptor molecule can be a carbohydrate, an oligosaccharide, a protein or glycoprotein, or a lipid or glycolipid, and can be, e.g., N-acetylglucosamine, N-acetyllactosamine, galactose, fucose, sialic acid, glucose, lactose or any combination thereof. Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by the nucleic acid from SEQ ID No. 1, or the amino acid sequence from SEQ ID No. 2.

Additionally, the alpha-1,2-fucosyltransferase polypeptide may be altered by additions or deletions of peptide sequences in order to modify its activity. For example, polypeptide sequences may be fused to the alpha-1,2-fucosyltransferase polypeptide in order to effectuate additional enzymatic activity. Alternatively, amino acids may be deleted to remove or modify the activity of the protein. The protein may be modified to lack alpha-1,2-fucosyltransferase enzymatic activity but yet retain its structural three-dimensional structure. Such modification would be useful in the development of antibodies against alpha-1,2-fucosyltransferase polypeptide.

In addition, alpha-1,2-fucosyltransferase gene products may include proteins or polypeptides that represent functionally equivalent gene products. Such an equivalent alpha-1,2-fucosyltransferase gene product may contain deletions, additions or substitutions of amino acid residues within the amino acid sequence encoded by the alpha-1,2-fucosyltransferase gene sequence described above, but which results in a silent change, thus producing a functionally equivalent alpha-1,2-fucosyltransferase gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Within the context of this invention, "functionally equivalent", as used herein, refers to a polypeptide capable of exhibiting a substantially similar in vivo activity as the endogenous alpha-1,2-fucosyltransferase gene product encoded by the alpha-1,2-fucosyltransferase gene sequence described above, as judged by any of a number of criteria, including but not limited to antigenicity, i.e., the ability to bind to an anti-alpha-1,2-fucosyltransferase antibody, immunogenicity, i.e., the ability to generate an antibody which is capable of binding an alpha-1,2-fucosyltransferase protein or polypeptide, as well as enzymatic activity.

Included within the scope of the invention are alpha-1,2-fucosyltransferase proteins, polypeptides, and derivatives (including fragments) which are differentially modified during or after translation. Furthermore, non-classical amino acids or chemical amino acid analogs can be introduced as a substitution or addition into the alpha-1,2-fucosyltransferase polypeptide sequence.

The alpha-1,2-fucosyltransferase polypeptide may be produced by recombinant DNA technology using techniques well known in the art. Methods which are well known to those skilled in the art can be used to construct expression vectors containing alpha-1,2-fucosyltransferase coding sequences and appropriate transcriptional translational control signals. These methods include, for example, in vitro recombinant DNA techniques, synthetic techniques, and in vivo genetic recombination. See, for example, the techniques described in Sambrook et al., Molecular Cloning: A Laboratory Manual, 2nd Ed., Cold Spring Harbor Laboratory Press, Cold Spring Harbor, N.Y. (1989).

"Oligosaccharide" as the term is used herein and as generally understood in the state of the art, refers to a saccharide polymer containing a small number, typically three to ten, of simple sugars, i.e. monosaccharides.

According to another aspect of the invention, a vector is provided, containing a nucleic acid sequence as given above encoding a polypeptide with alpha-1,2-fucosyltransferase activity, wherein the nucleic acid sequence is operably linked to control sequences recognized by a host cell transformed with the vector. In a particularly preferred embodiment, the vector is an expression vector, and, according to another aspect of the invention, the vector can be present in the form of a plasmid, cosmid, phage, liposome, or virus.

Also, the invention relates to host cells, containing a sequence consisting of the polynucleotide according to the invention and as described above, wherein the sequence is a sequence foreign to the host cell and wherein the sequence is integrated in the genome of the host cell. Thereby, "foreign to the host cell" means, that the sequence is not naturally occurring in said host cell, i.e. the sequence is heterologous with respect to the host cell. The heterologous sequence may be stably introduced, e.g. by transfection, transformation, or transduction, into the genome of the host cell, wherein techniques may be applied which will depend on the host cell the sequence is to be introduced. Various techniques are known to a person skilled in the art and are, e.g., disclosed in Sambrook et al., 1989, supra. Thus, the host cell the heterologous sequence has been introduced in, will produce the heterologous protein the polynucleotide according to the invention is coding for.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., Basic Methods in Molecular Biology, (1986), and Sambrook et al., 1989, supra.

Thus, the polynucleotide according to the invention, may, e.g., be comprised in a vector which is to be stably transformed/transfected into host cells. In the vector, the polynucleotide of the invention is under control of an, e.g., inducible promoter, so that the expression of the gene/polynucleotide can be specifically targeted, and, if desired, the gene may be overexpressed in that way.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above.

Accordingly, the present invention also relates to an isolated polypeptide with alpha-1,2-fucosyltransferase activity consisting of an amino acid sequence selected from the group consisting of:
 (a) the amino acid sequence shown in SEQ ID No.: 2;
 (b) an amino acid sequence of an allelic variant of the amino acid sequence shown in SEQ ID No. 2, wherein said allelic variant is encoded by a nucleic acid molecule that hybridizes under stringent conditions to the opposite strand of a nucleic acid molecule shown in SEQ ID No. 1;
 (c) an amino acid sequence of an ortholog of an amino acid sequence shown in SEQ ID No. 2, wherein said ortholog is encoded by a nucleic acid molecule that hybridizes under stringent conditions to the opposite strand of a nucleic acid molecule shown in SEQ ID No. 1; and
 (d) a fragment of the amino acid sequence shown in SEQ ID No. 2, wherein said fragment comprises at least 10 contiguous amino acids, and wherein said fragment has an alpha-1,2-fucosyltransferase activity.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15 C lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Exemplary stringent hybridization conditions can be as following: 50% formamide, 5×SSC, and 1% SDS, incubating at 42 C, or, 5×SSC, 1% SDS, incubating at 65 C, with wash in 0.2×SSC, and 0.1% SDS at 65 C.

Also, the invention refers to a host cell containing a vector as defined above, or containing the polynucleotide according to the invention as a heterologous sequence introduced in the host cell's genome, and in particular a host cell which is selected from the group consisting of fungi including yeast, bacteria, insect, animal and plant cells. It is particularly preferred if the host cell is an *Escherichia coli* cell.

As used herein, the term "host cell" is presently defined as a cell which has been transformed or transfected, or is capable of transformation or transfection by an exogenous polynucleotide sequence.

A variety of host-expression vector systems may be utilized to express the alpha-1,2-fucosyltransferase gene coding sequence of the invention. Such host-expression systems represent vehicles by which the coding sequence of interest may be produced and subsequently purified, but also represent cells which, when transformed or transfected with the appropriate nucleotide coding sequence, exhibit the alpha-1,2-fucosyltransferase gene product of the invention in situ.

A number of suitable expression systems and hosts can, e.g., be found in WO/0026383 and EP 1 243 647, which deal with an alpha-1,2-fucosyltransferase from *Helicobacter pylori*, the publication of which is explicitly referred to herewith.

According to another aspect of the invention, the nucleic acid encoding the polypeptide with alpha-1,2-fucosyltransferase activity is adapted to the codon usage of the respective cell.

The invention further relates to the use of a polynucleotide, the vector, or of the polypeptide according to the invention, respectively, for the production of a fucosylated oligosaccharide, (glyco)protein and/or (glyco)lipid.

Thereby, according to one aspect of the use, the production of said fucosylated oligosaccharide, (glyco)protein and/or (glyco)lipid is performed by means of a heterologous or homologous expression of the polynucleotide encoding the alpha-1,2-fucosyltransferase.

According to another aspect of the use, the fucosylated oligosaccharide is an oligosaccharide known from human milk, such as 2'-fucosyllactose.

The invention also relates to a method for producing fucosylated oligosaccharides, (glyco)proteins and (glyco)lipids, comprising the steps of:
 a. providing a polypeptide with alpha-1,2-fucosyltransferase activity according to the invention,
 b. contacting the polypeptide with alpha-1,2-fucosyltransferase activity of step a. with a mixture comprising a donor substrate comprising a fucose residue, and an acceptor substrate comprising a mono- or oligosaccharide, (glyco)protein or (glyco)lipid under conditions where the polypeptide catalyzes the transfer of a fucose residue from the donor substrate to the acceptor substrate, thereby producing a fucosylated oligosaccharide, (glyco)protein or (glyco)lipid.

According to the invention, the method for producing fucosylated oligosaccharides may be performed in a cell-free system or in a system containing cells. The substrates are allowed to react with the alpha-1,2-fucosyltransferase polypeptide for a sufficient time and under sufficient conditions to allow formation of the enzymatic product. It is to be understood, that these conditions will vary depending upon the amounts and purity of the substrate and enzyme, whether the system is a cell-free or cellular based system. These variables will be easily adjusted by those skilled in the art.

In cell-free systems, the polypeptide according to the invention, the acceptor substrate(s), donor substrate(s) and, as the case may be, other reaction mixture ingredients, including other glycosyltransferases and accessory enzymes are combined by admixture in an aqueous reaction medium. The enzymes can be utilized free in solution, or they can be bound or immobilized to a support such as a polymer and the substrates may be added to the support. The support may be, e.g., packed in a column.

Cell containing systems for the synthesis of fucosylated oligosaccharides may include recombinantly modified host cells.

Thus, the invention also relates to a method for producing fucosylated oligosaccharides, (glyco)proteins and (glyco)lipids, comprising the steps of:
 a. growing, under suitable nutrient conditions permissive for the production of the fucosylated oligosaccharide, (glyco)protein and/or (glyco)lipid, and permissive for the expression of a polypeptide with alpha-1,2-fucosyltransferase activity, a host cell as described above;
 b. providing, simultaneously or subsequently to step a., a donor substrate comprising a fucose residue and an acceptor substrate comprising an oligosaccharide, (glyco)protein or (glyco)lipid, so that the alpha-1,2-fucosyltransferase expressed in said host cell catalyzes the transfer of a fucose residue from the donor substrate to the acceptor substrate, thereby producing a fucosylated oligosaccharide, (glyco)protein or (glyco)lipid; and c. isolating said fucosylated oligosaccharide, (glyco)protein and/or (glyco)lipid from the host cell or the medium of its growth.

In the method according to the invention, the donor substrate may be GDP-fucose. It is particularly preferred if the donor substrate is GDP-fucose.

According to one aspect of the invention, the acceptor substrate is selected from N-acetylglucosamine, N-acetyllactosamine, galactose, fucose, sialic acid, glucose, lactose or any combination thereof. In particular, lactose is preferred as acceptor substrate.

The term "substrate", as used herein, means any material or combinations of different materials that may be acted upon by the polypeptide of the invention to give rise to fucosylated oligosaccharides, (glyco)proteins or (glyco)lipids.

The substrates are allowed to react with the alpha-1,2-fucosyltransferase polypeptide for a sufficient time and under sufficient conditions to allow formation of the enzymatic product. These conditions will vary depending upon the amounts and purity of the substrate and enzyme, whether the system is a cell-free or cellular based system. These variables will be easily adjusted by those skilled in the art.

According to one aspect of the method according to the invention, the donor substrate is provided in step b. by means of having it produced within the host cell. In doing so, an enzyme converting, e.g., fucose, which is to be added to the host cell, to GDP-fucose is simultaneously expressed in the host cell. This enzyme may be, e.g., a bifunctional fucose kinase/fucose-1-phosphate guanylyltransferase, like Fkp from *Bacteroides fragilis*, or the combination of one separate fucose kinase together with one separate fucose-1-phosphate guanylyltransferase like they are known from several species including *Homo sapiens*, *Sus scrofa* and *Rattus norvegicus*.

Alternatively, in step b., the donor substrate may be added to the culture medium/the host cells or be produced by the cells own metabolism.

In yet a further embodiment, the invention relates to a method comprising the following steps a) growing, host cells transformed or transfected to comprise a nucleic acid sequence selected from i) SEQ ID No. 1 from the enclosed sequence listing, ii) a nucleic acid sequence complementary to SEQ ID No. 1, and iii) nucleic acid sequences which hybridize under stringent conditions to the nucleic acid sequences defined in i) and ii) or their complementary strands, under suitable nutrient conditions so that the nucleic acid sequence selected from i), ii) and iii) are being expressed as a peptide having alpha-1,2-fucosyltransferase activity;

b) providing, simultaneously or subsequently to step a., a donor substrate comprising a fucose residue and an acceptor substrate comprising an oligosaccharide, (glyco)protein or (glyco)lipid, so that the alpha-1,2-fucosyltransferase expressed in said host cell catalyzes the transfer of a fucose residue from the donor substrate to the acceptor substrate, thereby producing a fucosylated oligosaccharide, (glyco)protein or (glyco)lipid; and c) isolating said fucosylated oligosaccharide, (glyco)protein and/or (glyco)lipid from the host cell or the medium of its growth.

In the methods according to the invention, the peptide which is expressed in the host cell, displays alpha-1,2-fucosyltransferase activity and, thus, transfers a fucose residue from a donor, e.g. guanosine-diphosphate fucose (GDP-fucose), to an acceptor, which include oligosaccharides, (glyco)proteins and (glyco)lipids. In that way, the thus fucosylated acceptor substrate may be used as food additive, for the supplementation of baby food, or as either therapeutically or pharmaceutically active compound. With the novel methods, fucosylated products can easily and effectively be provided, without the need for complicated, time and cost consuming synthetic processes.

As used herein, the term "isolating" means harvesting, collecting or separating from the gene expression system the product produced by the alpha-1,2-fucosyltransferase according to the invention.

Accordingly, the invention also relates to the fucosylated oligosaccharide, (glyco)protein and/or (glyco)lipid obtained by the methods according to the invention, as well as to the use of a polynucleotide, the vector or the polypeptide as described above for the production of fucosylated oligosaccharides, (glyco)proteins and/or (glyco)lipids.

According to yet another embodiment, the production of said fucosylated oligosaccharide, (glyco)protein and/or (glyco)lipid is performed by means of a heterologous or homologous (over)expression of the polynucleotide encoding the alpha-1,2-fucosyltransferase.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described above and below are those well known and commonly employed in the art. Standard techniques are used for nucleic acid and peptide synthesis. Generally, enzymatic reactions and purification steps are performed according to the manufacturer's specifications.

The invention also covers fragments of the polynucleotide sequences disclosed therein.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

BRIEF DESCRIPTION OF THE DRAWINGS

Several embodiments of the invention are illustrated in the figures and explained in more detail in the following description. In the figures:

FIG. 1A shows the DNA and the amino acid sequence of the gene coding for alpha-1,2-fucosyltransferase WbgL from *E. coli* O126;

Figure 2:
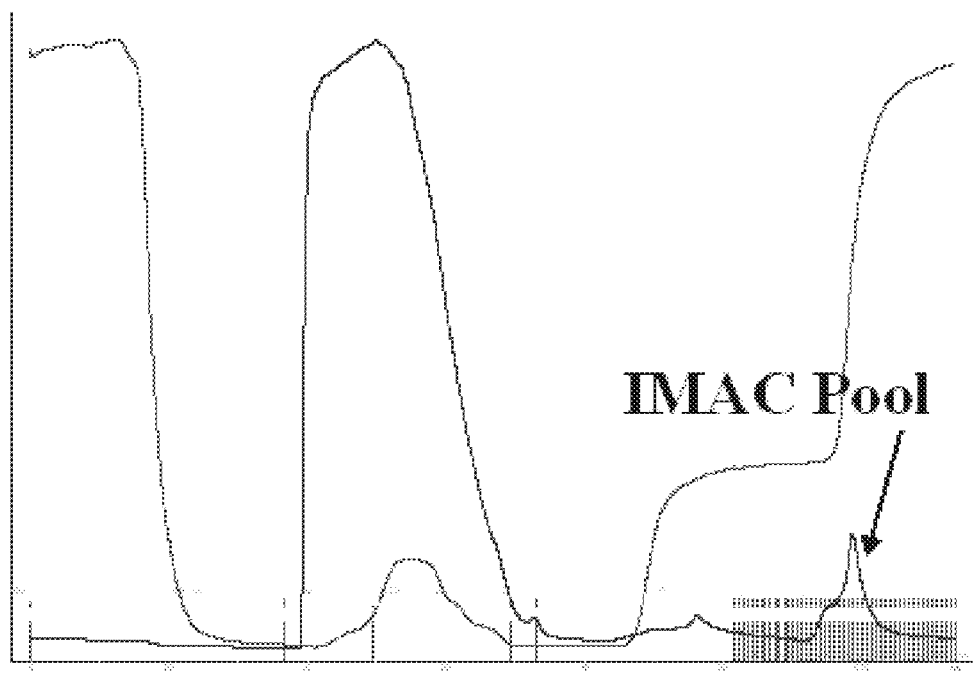
Figure 3:
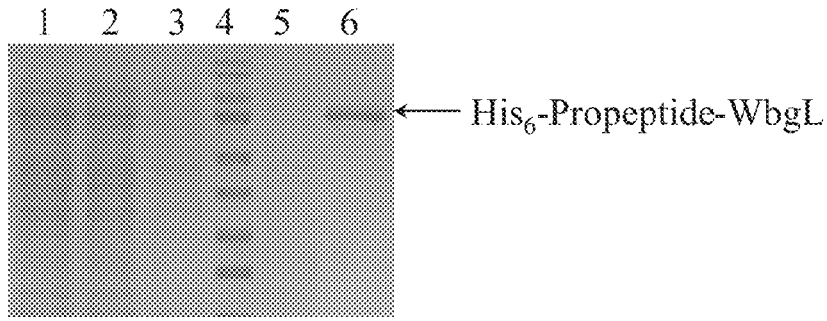
Figure 4:
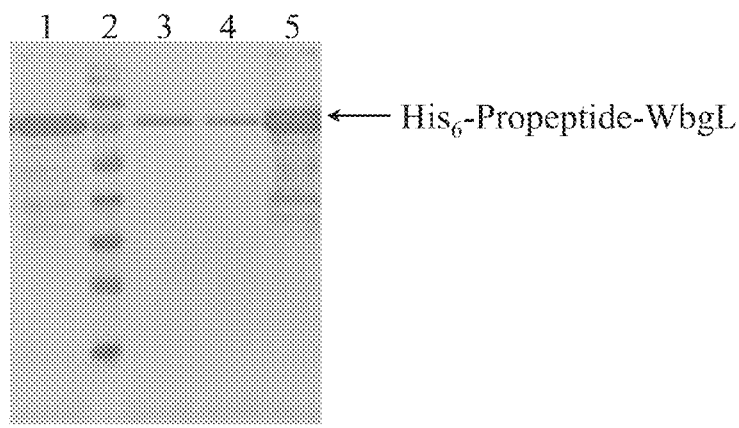
Figure 5:
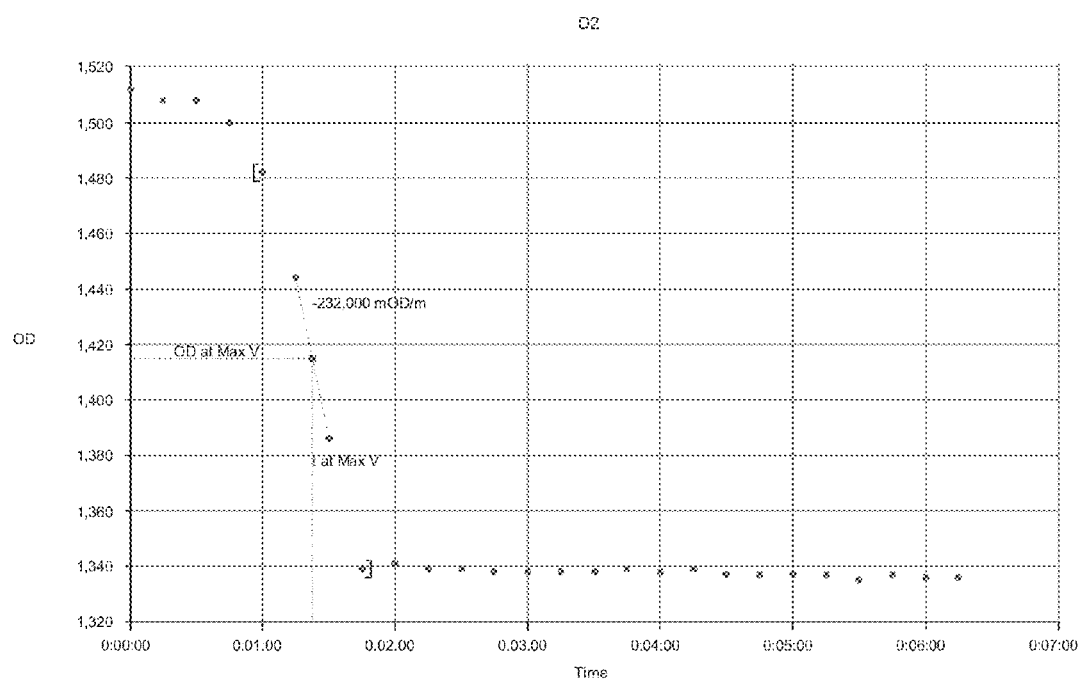
Figures 6A, 6B:
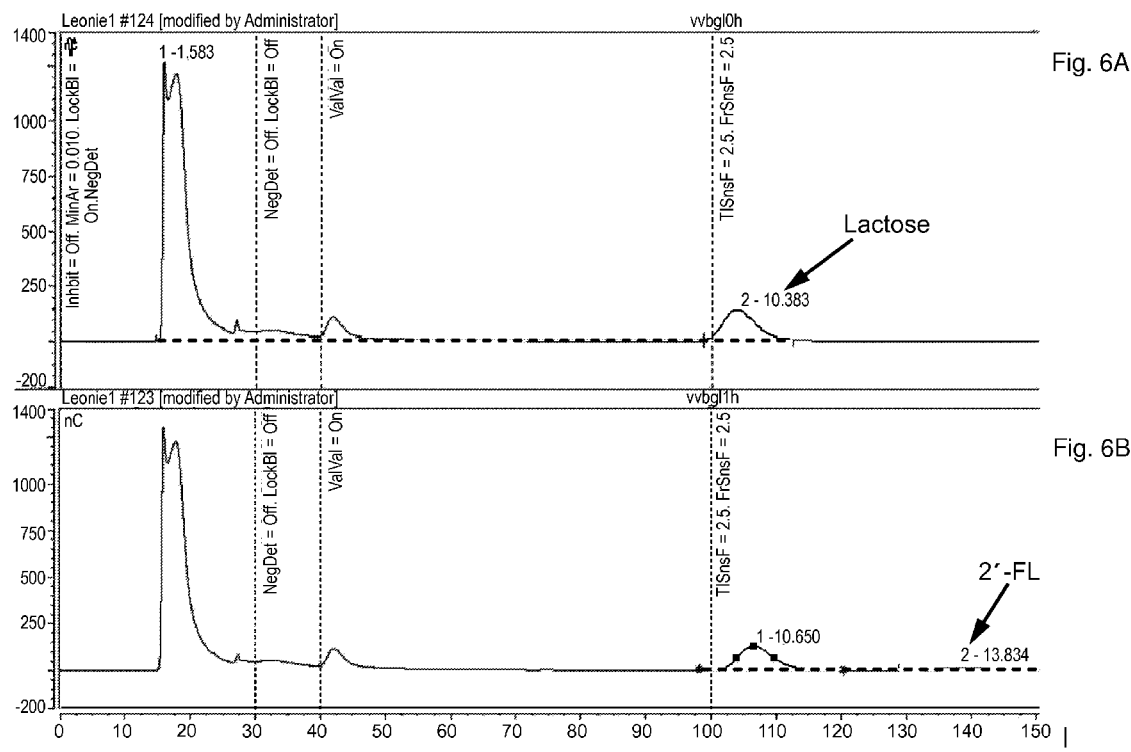
Figure 8:
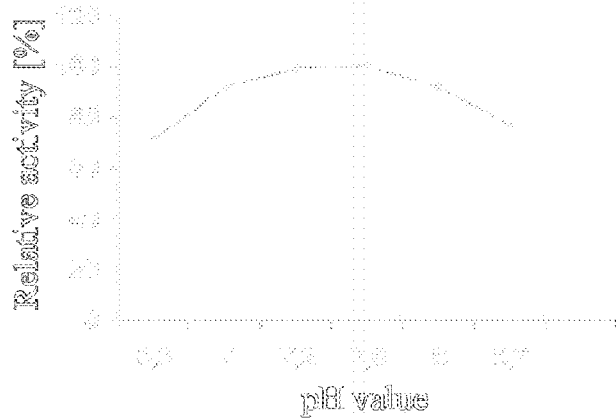
Figure 9:
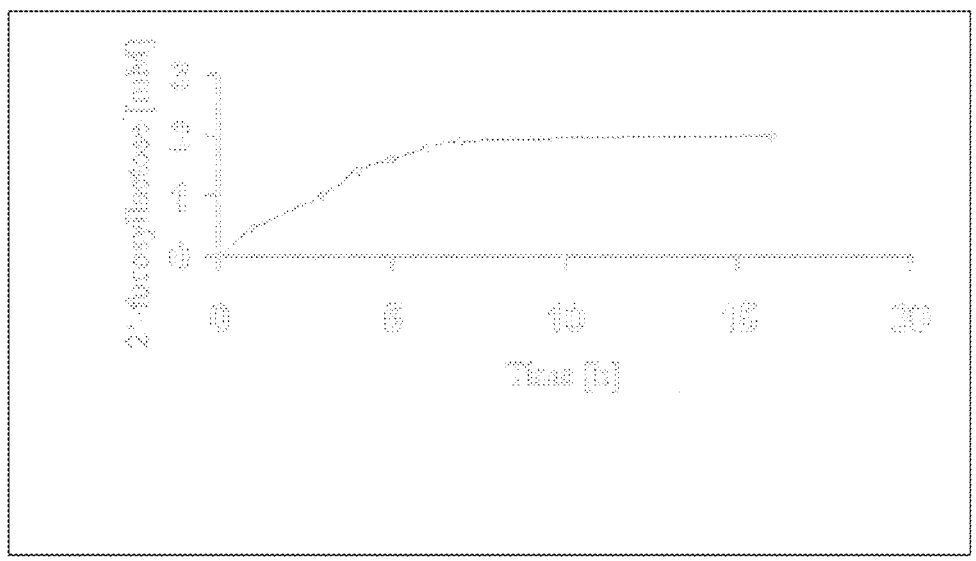
Figure 11:
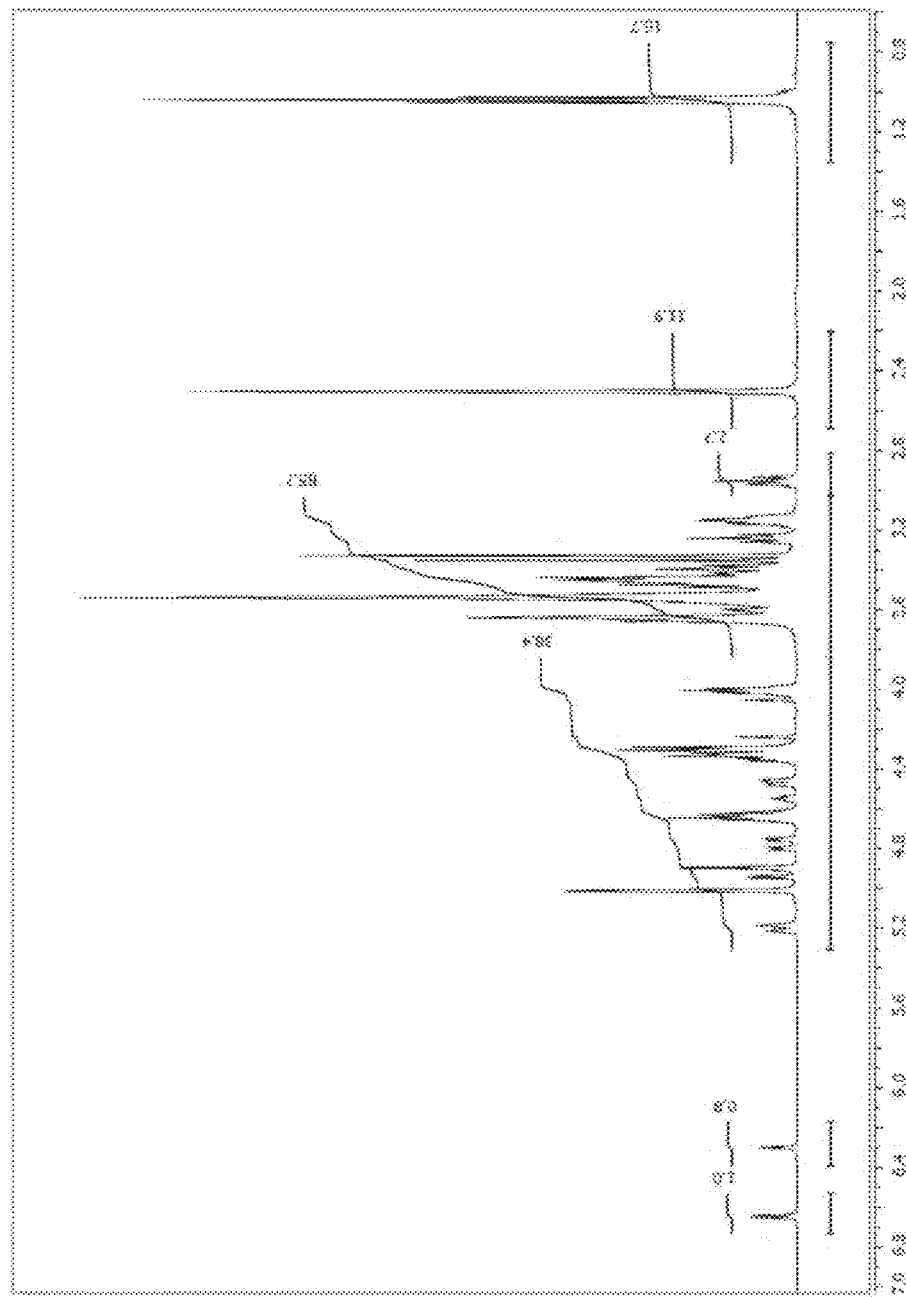

FIG. 2 shows the chromatogram of WbgL purification by IMAC $Ni^{2+-}$ NTA Sepharose column (blue: absorption at 280 nm, red: conductivity; fractions containing $His_6$-Propeptide-WbgL eluting from the column are called IMAC pool);

FIG. 3 shows SDS-PAGE analysis of $His_6$-Propeptide-WbgL expression in crude extract and insoluble fractions of E. coli JM109(DE3) pET22bHIS6PropwbgL as well as in wash fractions of purification of $His_6$-Propeptide-WbgL and of purified $His_6$-Propeptide-WbgL;

FIG. 4 shows detection of $His_6$-Propeptide-WbgL on an immunoblot using a monoclonal anti-$His_6$-antibody conjugated to horse radish peroxidase (HRP) (Roche Diagnostics, Mannheim, Germany) after incubation with DAB substrate (Roche Diagnostics, Mannheim, Germany);

FIG. 5 shows the continuous photometric assay of purified $His_6$-Propeptide-WbgL with 0.4 mM GDP-β-L-fucose and 5 mM lactose in which activity can be detected by decrease of absorption at 340 nm caused by oxidation of NADH;

FIG. 6 shows detection of 2'-fucosyllactose production from WbgL reaction by HPAEC-PAD at start of reaction where no 2' fucosyllactose is present (A); and 2'-fucosyllactose produced after 1 hour of WbgL reaction with 2 mM GDP-beta-L-fucose and 5 mM lactose (B);

FIG. 7 shows the analysis of reaction mixture started with 2 mM GDP-fucose and 5 mM lactose and WbgL by capillary electrophoresis at the beginning of the reaction where only GDP-β-L-fucose can be detected (A); and after 16 hours of reaction where only guanosine as degradation product of GDP released by WbgL activity can be detected (B);

FIG. 8 shows relative activity of WbgL at different pH values (pH 6.8 to 8.4) in 50 mM Tris-HCl buffer;

FIG. 9 shows the increase of 2'-fucosyllactose concentration as measured in a WbgL reaction started with 2 mM GDP-beta-L-fucose and 5 mM lactose at different time points during 16 hours of reaction process;

FIG. 10 shows HPLC chromatogram; separation by Phenomenex Rezex RCM Ca2+ column with water as eluent (0.6 ml/min for 30 minutes at 80° C.) and detection by refractive index detector (Shimadzu, Germany) (A); and the HPLC chromatogram; separation by Reprosil Carbohydrate column, 5 μm, 250×4.6 mm, with acetonitrile/water (68:32) as eluent (1.4 ml/min for 20 minutes at 35° C.; detection by refractive index detector (Shimadzu, Germany)) (B);

FIG. 11 shows the NMR spectrum of 2'-fucosyllactose produced by WbgL.

DESCRIPTION OF PREFERRED EMBODIMENTS

Example

Cloning of the Gene

Figure 1B:
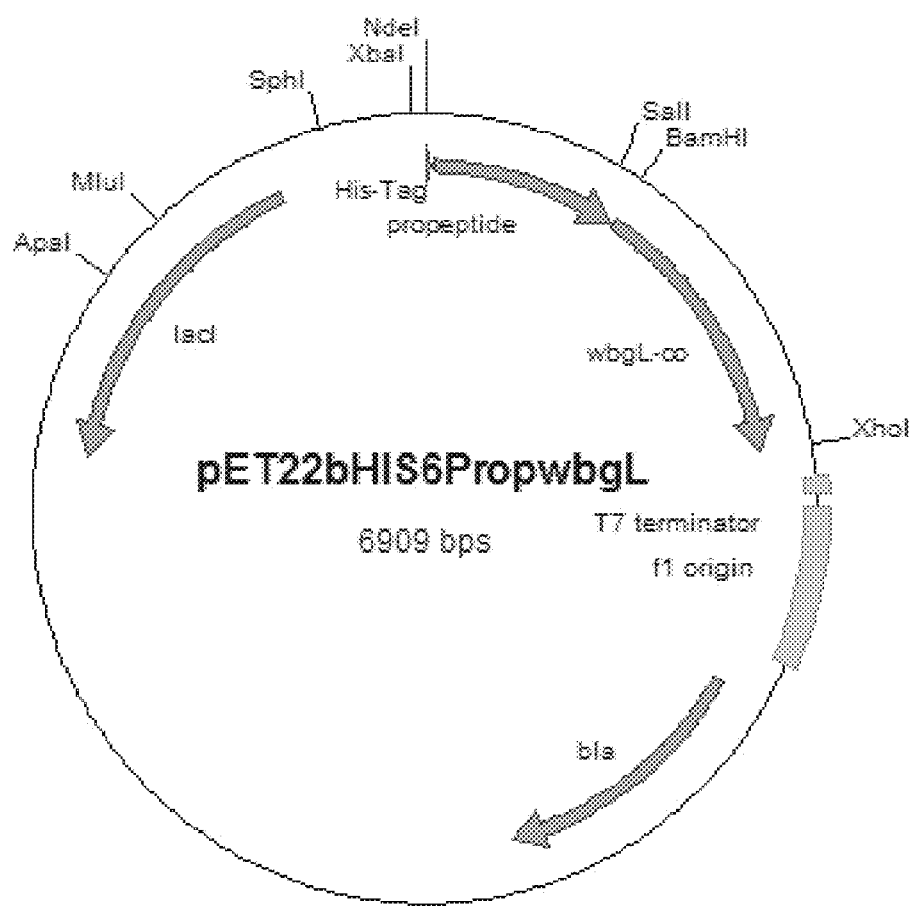
FIG. 1B shows the vector map of pET22bHIS6PropwbgL, i.e. codon optimized gene wbgL from *Escherichia coli* O126 encoding the new alpha-1,2-fucosyltransferase WbgL cloned into pET22b(+) (Novagen, Darmstadt, Germany, via BamHI/XhoI) to which 18 bp coding for an N-terminal His-Tag and 621 bp from the propeptide of *Staphylococcus hyicus* lipase were added previously via NdeI/BamHI (description see below)
Figure 1C:
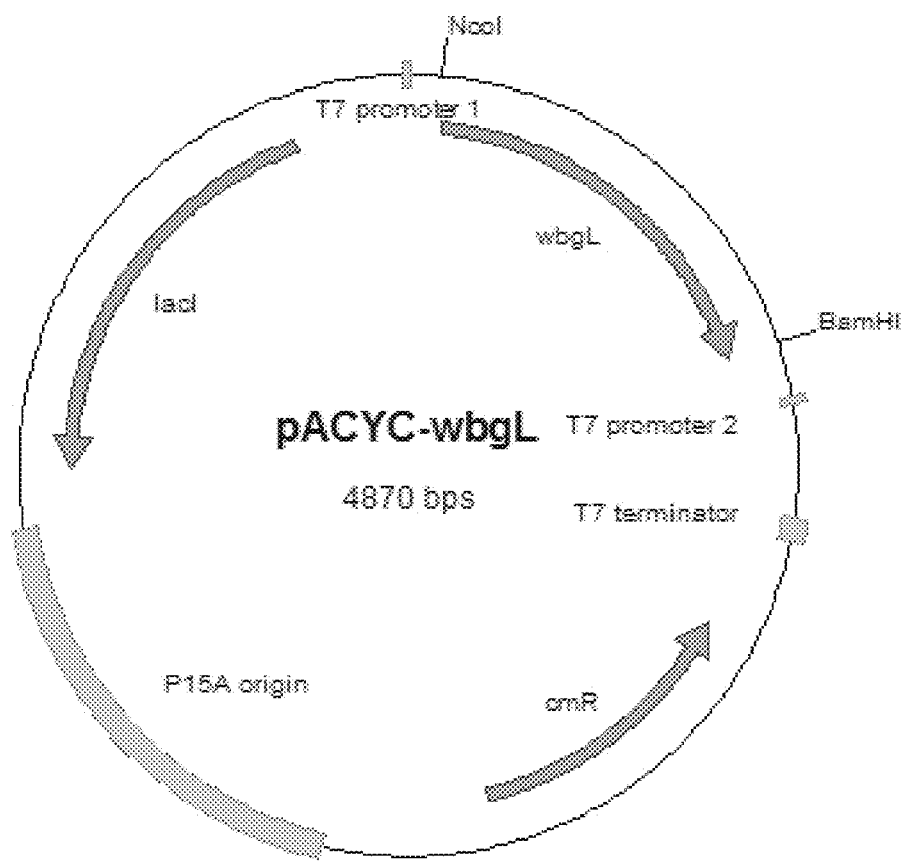
FIG. 1C shows the vector map of pACYC-wbgL, i.e. codon optimized gene wbgL from *Escherichia coli* O126 encoding the new alpha-1,2-fucosyltransferase WbgL cloned into pACYCDuet-1 (Novagen via NcoI/BamHI)

For cytoplasmatic expression of the putative alpha-1,2-fucosyltransferase WbgL the expression vector pET22b(+) (Novagen, Darmstadt, Germany) was modified. Therefore, the pelB leader sequence leading to periplasmatic expression in E. coli was cut off using the restriction enzymes NdeI and BamHI. The propeptide gene sequence (SEQ ID No. 3) of the lipase of S. hyicus (Sauerzapfe, B., D. J. Namdjou, et al. (2008): "Characterization of recombinant fusion constructs of human beta-1,4-galactosyltransferase 1 and the lipase pre-propeptide from Staphylococcus hyicus." Journal of Molecular Catalysis B: Enzymatic 50(2-4): 128-140) was amplified from the plasmid pLGalTΔ38 using the primers 5'-CATATGCACCACCACCACCACCACCACAATGATTC-GACAACACAAACAACGAC-3' (SEQ ID No. 5) and 3'-GGATCCGTATGGTTTTTTGTCGCTCGCTTG-5' (SEQ ID No. 6), and fused to the modified pET22b vector resulting in vector pET22bHIS6Prop. The resulting vector was digested by BamHI and XhoI. The gene coding for putative alpha-1,2-fucosyltransferase WbgL from E. coli O126 was synthesized by Geneart (Regensburg, Germany) including the restriction sites BamHI and XhoI. Ligation into the vector pET22bHIS6Prop gave the expression vector pETHIS6PropwbgL (see FIG. 1A), which produces $His_6$-Propeptide-WbgL (513 amino acids) in the cytoplasm of E. coli after induction with isopropyl thiogalactoside (IPTG). Alternatively, gene wbgL was cloned via NcoI/BamHI into vector pACYCDuet-1 (Novagen, Darmstadt, Germany) after amplification using primers 5'-GATCACCATGGGCA-GCATTATTCGTCTGCAGGGTGGTC-3' (SEQ ID No. 7) and 5'-GATCAGGATCCTTAGCAGCTGCTATGTTTAT-CAACGTTGATCC-3' (SEQ ID No. 8), to yield vector pACYC-wbgL (see FIG. 1B). For propagation of plasmids E. coli Nova Blue (Novagen, Darmstadt, Germany) or E. coli TOP10 (Invitrogen, Darmstadt, Germany) and for expression of $His_6$-Propeptide-WbgL E. coli JM109(DE3) (Promega®, Madison, USA) were used.

Cultivation and Expression of Fucosyltransferases

Transformants were grown in 100 ml Erlenmeyer flasks containing 20 ml LB medium with 100 μg/mL ampicillin and incubated overnight at 37° C. and 130 rpm. For protein production cells were grown in 5 L Erlenmeyer flasks with 1000 mL TB-medium at 37° C. and 80 rpm. The induction of the lacZ promoter was carried out by adding IPTG to a final concentration of 0.1 mM to the cultures ($OD_{600}$=0.6-0.8). Incubation was continued for 20 h at 25° C. and the cells were finally harvested by centrifugation.

Enzyme Purification

A 40% (w/w) cell suspension of the E. coli cells in 50 mM Tris-HCl buffer pH 7.6 was disrupted by sonication (4×15 s). After centrifugation (15000 rpm, 30 min) the pellets were preserved for the analysis of the production of inclusion bodies by SDS-PAGE. The crude extract (15 mL) was loaded on an IMAC column (0.8 $cm^2$×10 cm, 1.5 mL/min) using $Ni^{2+-}$NTA sepharose (Qiagen®, Hilden, Germany), which was previously equilibrated with 100 mL 50 mM Tris-HCl pH 7.6 (buffer A). After a washing step with buffer B containing 0.3 M NaCl and 20 mM imidazole proteins were eluted by a concentration of 300 mM imidazole in buffer C (50 mM Tris-HCl pH 7.6, 0.3 M NaCl and 300 mM imidazole). All fractions were analysed for protein concentration and assayed for enzyme activity. All fractions containing active soluble WbgL from elution with buffer C were pooled and the resulting solution was called IMAC pool (see FIG. 2).

SDS-PAGE and Detection Via Western Blot

Expression of $His_6$-Propeptide-WbgL was monitored by SDS-PAGE and Western-blot. Therefore SDS-PAGE analysis was performed with 10% acrylamide gels casted according to the gel casting instructions of Invitrogen® (Invitrogen®, Paisley, UK). Protein samples (40 μg) were loaded onto each slot of the gel. Prestained Protein Ladder PageRuler™ (Fermentas®, Vilnius, Lithuania) was used for the determination of the molecular mass. The protein gels were stained with Coomassie Blue (see FIG. 3).

An immunoblot was performed using a specific anti-$His_6$-antibody in order to detect $His_6$PropWbgL. Therefore samples of cell debris of E. coli JM109(DE3), crude extract and IMAC fractions of His$_6$-Propeptide-WbgL were separated on SDS-PAGE gels and transferred onto PVDF membranes by the NuPAGE Western transfer protocol (BioRad, München, Germany). Membranes were blocked with 3% BSA in TBS buffer (10 mM Tris-HCl, 150 mM NaCl, pH 7.2). A monoclonal anti-His$_6$-antibody conjugated to horse radish peroxidase (HRP) (Roche Diagnostics, Mannheim, Germany) was used for specific binding. After a washing step with TBS buffer containing 0.1% Tween 20 the blots were incubated with DAB substrate (Roche Diagnostics, Mannheim, Germany) and the HRP reaction was stopped by removal of the solution and addition of distilled water (see FIG. 4).

Activity Assays

Enzyme activities of His$_6$-Propeptide-WbgL in the crude extract and IMAC fractions were determined by a photometric assay and HPAEC-PAD analysis of 2' fucosyllactose.

The photometric assay was performed using the pyruvate kinase/lactate dehydrogenase system for the detection of released GDP (Barratt, D. H., L. Barber, et al. (2001). "Multiple, distinct isoforms of sucrose synthase in pea." Plant Physiology 127(2): 655-664.). The reaction mixture for the microtiter plate assay contained 50 mM Tris-HCl pH 7.6, 2 mM GDP-beta-L-fucose, 5 mM lactose, 1 mM phosphoenolpyruvate, 1 mM DTT, 0.25 mM NADH, 2 mM MnCl$_2$, 5 U pyruvate kinase, and 5 U lactate dehydrogenase in a total volume of 250 µl. The reaction was started by addition of 100 µl enzyme solution and followed at 340 nm at 30° C. Control experiments for the detection of side activities were done without acceptor substrate lactose (see FIG. 5).

Enzyme activity was also determined by HPAEC-PAD analysis for detection of 2'-fucosyllactose. The assay solution contained 2 mM GDP-β-L-fucose, 5 mM lactose, 50 mM Tris-HCl pH 7.6 with 2 mM MnCl$_2$, 1 mM DTT, 1 U alkaline phosphatase in a total volume of 175 µl and was incubated at 30° C. after the addition of 175 µl crude extract and purified enzyme solution. The reaction was stopped by heating for 5 min at 95° C. at different time points where the conversion rate was linear. The centrifuged samples were analysed by Dionex HPAEC-PAD (Dionex Corporation, Sunnyvale, Calif., USA) on CarboPac PA1 column using Chromeleon™ 6.40 Software. The elution was carried out with 50 mM NaOH at 30° C. (flow rate 1 mL/min, 50 µL injection volume). The concentration of the generated trisaccharide 2'-fucosyllactose was determined by a standard calibration curve with commercially available 2'-fucosyllactose and used for subsequent calculation of enzyme activity (see FIG. 6).

For both, HPAEC-PAD and photometric assays, 1 U of His$_6$-Propeptide-WbgL is the amount of enzyme which produces 1 µmol product (GDP or 2'-fucosyllactose) per minute under standard assay conditions.

GDP-beta-L-fucose and its consumption was analysed by capillary electrophoresis on a P/ACE MDQ apparatus from Beckman Coulter (Krefeld, Germany), equipped with a UV detector. The samples for the determination of the activated donor substrate GDP-beta-L-fucose were stopped by heating (95° C.) for 5 min and centrifuged for 10 min at 15000 rpm (Rotina 35R, Hettich, Tuttlingen, Germany). The detection was accomplished on an untreated fused-silica capillary (I.D. 75 mm, 57 cm total capillary length, 50 cm to the detector) with 50 mM Na$_2$B$_4$O$_7$×10 H$_2$O/64 mM boric acid buffer, pH 8.9. Conditions for migration and detection were 25 kV (23 mA) at 25.8° C. and UV detection at 254 nm, respectively. Samples were injected by pressure (5.0 sec at 0.5 psi in the forward direction) (see FIG. 7). The identities of GDP-beta-L-fucose and the generated guanosine were confirmed with commercially available substrates.

pH Optimum and Metal Ion Dependency

To study the optimal pH value for the activity of recombinant His$_6$-Propeptide-WbgL, assays were performed at different pH values of a 50 mM Tris-HCl buffer ranging from pH 6.8 to 8.4. Optimal pH value was 7.6 (see. FIG. 8). Addition of metal ions Mn$^{2+}$ to standard assays allowed to investigate the metal ion dependency. All samples were analyzed HAPAEC-PAD as described above. It was shown, that the enzyme was not dependent on Mn$^{2+}$ ions.

Kinetic Analysis

The kinetic constants of His$_6$-Propeptide-WbgL for the acceptor substrate lactose and the donor substrate GDP-beta-L-fucose were derived from initial rate analysis at a variable substrate concentrations using the photometric assay described above. GDP-beta-L-fucose was varied from 0.02 mM to 4 mM at a constant concentration of 10 mM lactose and lactose was altered from 0.05 to 40 mM at a constant concentration of 2 mM GDP-beta-L-fucose. All data were determined by non linear-regression analysis according to the Michaelis-Menten equation using the Sigma Plot 10 software (SPSS Science Software GmbH, Erkrath, Germany).

TABLE 1

Kinetic constants of recombinant alpha-1,2-fucosyltransferase His6-Propeptide-WbgL

| Substrate | Km value [mM] | Vmax [mU/mg] | Vmax/Km [mU*mg$^{-1}$ *mM$^{-1}$] | $R^2$ |
|---|---|---|---|---|
| Lactose | 5.3 | 170 | 32 | 0.9935 |
| GDP-Fucose | 0.27 | 167 | 618 | 0.9907 |

Acceptor Substrate Spectrum Studies

The substrate spectrum of recombinant His$_6$-Propeptide-WbgL was analysed by HPAEC-PAD according to activity assay described above. Instead of 5 mM lactose different acceptor substrates were tested to determine the relative activity compared to lactose.

TABLE 2

Acceptor spectrum of alpha-1,2-fucosyltransferase His6-Propeptide-WbgL

| Substrate | Relative activity [%] |
|---|---|
| Lactose | 100 |
| Lactulose | 124 |
| LacNAc Typ I | 28 |
| LacNAc Typ II | 95 |
| D-Galactose | 71 |
| 3-Fucosyllactose | 0 |
| β-Benzyl-Lactose | 50 |
| D-GalNAc | 0 |
| D-GalNH$_2$ | 0 |
| LacDiNAc | 0 |

Production of Fucosylated Compounds

Cells E. coli BL21(DE3) ΔlacZ pDEST14-fkp pCOLA-lacY-fucP were transformed with pACYCDuet-1 carrying the appropriate fucosyltransferase gene. Colonies were grown on 2YT plates with the appropriate antibiotics. 5 ml over night cultures (2YT with antibiotics) were grown of each strain and from this cultures 15 ml mineral medium each were inoculated to 1%. Cells were grown using glycerol as carbon source and at OD600=0.5 were induced with 0.1 mM IPTG and 40 mM lactose and 30 mM fucose were added. Cultures were incubated at 30° C. and 120 rpm. Production of 2'-fucosyllactose was monitored HPLC analysis. The comparison of the amount of 2'-fucosyllactose (2'-FL) produced by expression of FucT2 from *Helicobacter pylori* compared to the expression of WbgL from *Escherichia coli* O126 is shown in the following table 1:

TABLE 3

Comparison of the amount of 2'-fucosyllactose yield using alpha-1,2-fucosyltransferases FucT2 from *Helicobacter pylori* and WbgL from *Escherichia coli* O126

| Fucosyltransferase | Yield 2'-FL [mM] |
|---|---|
| without (negative control) | 0.00 |
| FucT2 (*Helicobacter pylori*) | 2.01 |
| WbgL (*Escherichia coli* O126) | 4.05 |

As can be seen from table 1, the amount of the fucosylated product 2'-fucosyllactose was significantly higher when using the alpha-1,2-fucosyltransferase according to the invention, i.e. WbgL from *Escherichia coli* O126, compared to the alpha-1,2-fucosyltransferase FucT2 from *Helicobacter pylori*, which is state of the art.

Purification of the Fucosylation Product

2'-fucosyllactose produced as described above was purified in several steps. First step was the purification by adsorption on activated charcoal. Culture supernatant from the production step was applied to a bed of activated charcoal. Flow-through was collected and analyzed, but no remaining 2'-fucosyllactose was detected. For removal of unspecifically bound medium compounds such as e.g. salts and amino acids the bed was washed with distilled water (no 2'-FL in flow-through). 2'-FL and remaining lactose and fucose were then eluted with 96% ethanol. Ethanol was subsequently evaporated in a rotary evaporator and the residue filtrated via 10 kDa crossflow module (Microdyn Nadir, Germany). Remaining salts were removed by electrodialysation and thereafter endotoxins were removed by filtration using a cross-flow module (Pall, Germany). 2'-FL was then separated from lactose and fucose in gram scale using gel permeation chromatography material Biogel P-2 (BioRad, Germany) packed into a 520 mm×428 mm glass column with frit. Purification of 2'-FL was monitored by thin layer chromatography. Fractions containing only 2'-fucosyllactose were pooled and freeze-dried.

Confirmation of the Identity of the Product

Purified 2'-fucosyllactose produced using the fucosyltransferase presented in this invention was analyzed by $^1$H-NMR (see FIG. 11). The resulting spectrum was consistent with the spectrum received for 2'-FL standard (Dextra, Reading, UK). In addition to that, different HPLC methods were applied to verify the identity of the resulting 2'-FL. HPAEC-PAD was applied as described above. Other methods were the separation using Phenomenex Rezex RCM Ca2+ column with water as eluent (0.6 ml/min for 30 minutes at 80° C.; detection by refractive index detector (Shimadzu, Germany)) (see FIG. 10A) and separation using Reprosil Carbohydrate, 5 μm, 250×4.6 mm, with acetonitrile/water (68:32) as eluent (1.4 ml/min for 20 minutes at 35° C.; detection by refractive index detector (Shimadzu, Germany)) (see FIG. 10B).

What is claimed is:

1. A method for producing fucosyllactose comprising the steps of:
   a) providing a polypeptide with alpha-1,2-fucosyltransferase activity comprising the amino acid sequence shown in SEQ ID NO: 2, wherein the polypeptide can transfer a fucose residue to a monosaccharide or an oligosaccharide that comprises lactose; and
   b) contacting the polypeptide with alpha-1,2-fucosyltransferase activity of step a) with a mixture comprising a donor substrate, wherein the donor substrate is GDP-fucose, and an acceptor substrate comprising a mono- or oligosaccharide comprising lactose under conditions wherein the polypeptide catalyzes the transfer of a fucose residue from the donor substrate to the acceptor substrate, thereby producing the fucosyllactose.

2. A method for producing fucosyllactose comprising the steps of:
   a) growing, under suitable nutrient conditions permissive for the production of the fucosylated oligosaccharide, and permissive for the expression of a polypeptide with alpha-1,2-fucosyltransferase activity, a host cell, wherein the host cell comprises a polynucleotide encoding a polypeptide with alpha-1,2-fucosyltransferase activity wherein the polynucleotide is selected from the group consisting of (i) the nucleic acid sequence shown in SEQ ID NO: 1, or (ii) a nucleic acid sequence complementary to SEQ ID NO: 1, wherein the polynucleotide is foreign to the host cell and wherein the polynucleotide is integrated in the genome of the host cell or wherein the host cell comprises a vector comprising the polynucleotide operably linked to control sequences recognized by the host cell transformed with the vector;
   b) providing, simultaneously or subsequently to step a), a donor substrate wherein the donor substrate is a GDP-fucose residue, and an acceptor substrate comprising a mono- or oligosaccharide comprising lactose, in order for the alpha-1,2-fucosyltransferase polypeptide to catalyze the transfer of a fucose residue from the donor substrate to the acceptor substrate, thereby producing fucosyllactose; and
   c) isolating said fucosyllactose from the host cell or the medium of its growth.

3. The method according to claim 2, wherein the GDP-fucose residue is provided by an enzyme simultaneously expressed in the host cell or by the metabolism of the host cell.

4. The method of claim 2, wherein the fucosyllactose is 2'-fucosyllactose.

5. A method for producing a fucosyllactose comprising expressing a polynucleotide encoding a polypeptide with alpha-1,2-fucosyltransferase activity, comprising:
   contacting a host cell comprising a polynucleotide encoding a polypeptide with alpha-1,2-fucosyltransferase activity with a donor substrate,
   wherein the polynucleotide is selected from the group consisting of a) the nucleic acid sequence shown in SEQ ID NO: 1, or b) a nucleic acid sequence complementary to SEQ ID NO: 1,
wherein the polynucleotide is foreign to the host cell and wherein the polynucleotide is integrated in the genome of the host cell or wherein the host cell comprises a vector comprising the polynucleotide operably linked to control sequences recognized by the host cell transformed with the vector, and
wherein the donor substrate comprises a GDP-fucose residue or is GDP-fucose.

6. The method according to claim 5, wherein the GDP-fucose residue is provided by an enzyme simultaneously expressed in the host cell or by the metabolism of the host cell.

7. The method of claim 5, wherein the fucosyllactose is 2'-fucosyllactose.

8. The method of claim 2, wherein the host cell is selected from the group consisting of fungal, yeast, bacteria, insect, animal and plant cells.

9. The method of claim 2, wherein the host cell is an *Escherichia coli* cell.

10. The method of claim 2, wherein the nucleic acid sequence encoding the polypeptide with alpha-1,2-fucosyltransferase activity is adapted to the codon usage of the cell.

11. The method of claim 2, wherein the polynucleotide encoding a polypeptide with alpha-1,2-fucosyltransferase activity comprises the nucleic acid sequence set forth as SEQ ID NO: 1.

12. A method for producing fucosyllactose comprising the steps of:
a) growing, under suitable nutrient conditions permissive for the production of the fucosylated oligosaccharide, permissive for the expression of a polypeptide with alpha-1,2-fucosyltransferase activity, a host cell with the ability to transfer a fucose residue to a mono- or oligosaccharide comprising lactose, wherein the host cell expresses a polypeptide with alpha-1,2-fucosyltransferase activity and the ability to transfer a fucose residue to a mono- or oligosaccharide comprising lactose, wherein the polypeptide comprises the amino acid sequence shown in SEQ ID NO: 2;

b) providing, simultaneously or subsequently to step a), a donor substrate wherein the donor substrate is a GDP-fucose residue, and an acceptor substrate comprising a mono- or oligosaccharide comprising lactose, in order for the alpha-1,2-fucosyltransferase polypeptide to catalyze the transfer of a fucose residue from the donor substrate to the acceptor substrate, thereby producing fucosyllactose; and c) isolating said fucosyllactose from the host cell or the medium of its growth.

13. The method of claim 12, wherein the polypeptide with alpha-1,2-fucosyltransferase activity consists of the amino acid sequence shown in SEQ ID NO: 2.

14. The method of claim 1, wherein the polypeptide with alpha-1,2-fucosyltransferase activity consists of the amino acid sequence shown in SEQ ID NO: 2.

15. The method of claim 5, wherein the host cell is an *Escherichia coli* cell.

16. The method of claim 12, wherein the host cell is an *Escherichia coli* cell.

* * * * *

SEQUENCE LISTING

```
<160> NUMBER OF SEQ ID NOS: 8

<210> SEQ ID NO 1
<211> LENGTH: 894
<212> TYPE: DNA
<213> ORGANISM: Escherichia coli

<400> SEQUENCE: 1
atgagcatta ttcgtctgca gggtggtctg ggtaatcagc tgtttcagtt tagctttggt      60
tatgccctga gcaaaattaa tggtacaccg ctgtatttcg acattagcca ttatgccgaa     120
aacgatgatc atggtggtta tcgtctgaat aatctgcaga ttccggaaga atatctgcag     180 tattatacc cgaaaattaa taatttat aaactgctgg tgcgtggcag ccgtctgtat        240
ccggatattt ttctgtttct gggcttttgc aacgaatttc atgcctatgg ctacgatttt     300
gaatatattg cccagaaatg gaaaagcaaa aaatacattg gctactggca gagcgaacac     360
ttttttcata aacatattct ggacctgaaa gaatttttta ttccgaaaaa tgtgagcgaa     420
caggcaaatc tgctggcagc aaaaattctg gaaagccaga gcagcctgag cattcatatt     480
cgtcgtggcg attatattaa aaacaaaacc gcaaccctga cacatggtgt ttgtagcctg     540
gaatattata aaaagccct gaacaaaatc cgcgatctgg caatgattcg tgatgtgttt     600
atctttagcg acgatatctt ctggtgcaaa gaaaatattg aaaccctgct gagcaaaaaa     660
tataatattt attatagcga agatctgagc caagaagagg atctgtggct gatgagcctg     720
gcaaatcatc atattattgc caatagcagc tttagttggt ggggtgcata tctgggtagc     780
agcgcaagcc agattgttat ttatccgacc ccgtggtatg atattacccc gaaaaacacc     840
tatatcccga ttgtgaacca ttggatcaac gttgataaac atagcagctg ctaa          894
```

<210> SEQ ID NO 2
<211> LENGTH: 297
<212> TYPE: PRT
<213> ORGANISM: Escherichia coli

<400> SEQUENCE: 2

Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
            20                  25                  30

Phe Asp Ile Ser His Tyr Ala Glu Asn Asp Asp His Gly Gly Tyr Arg
        35                  40                  45

Leu Asn Asn Leu Gln Ile Pro Glu Glu Tyr Leu Gln Tyr Tyr Thr Pro
    50                  55                  60

Lys Ile Asn Asn Ile Tyr Lys Leu Leu Val Arg Gly Ser Arg Leu Tyr
65                  70                  75                  80

Pro Asp Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
            100                 105                 110

Ile Gly Tyr Trp Gln Ser Glu His Phe His Lys His Ile Leu Asp
        115                 120                 125

Leu Lys Glu Phe Phe Ile Pro Lys Asn Val Ser Glu Gln Ala Asn Leu
    130                 135                 140

Leu Ala Ala Lys Ile Leu Glu Ser Gln Ser Ser Leu Ser Ile His Ile
145                 150                 155                 160

Arg Arg Gly Asp Tyr Ile Lys Asn Lys Thr Ala Thr Leu Thr His Gly
                165                 170                 175

Val Cys Ser Leu Glu Tyr Tyr Lys Lys Ala Leu Asn Lys Ile Arg Asp
            180                 185                 190

Leu Ala Met Ile Arg Asp Val Phe Ile Phe Ser Asp Ile Phe Trp
        195                 200                 205

Cys Lys Glu Asn Ile Glu Thr Leu Leu Ser Lys Lys Tyr Asn Ile Tyr
    210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
                245                 250                 255

Tyr Leu Gly Ser Ser Ala Ser Gln Ile Val Ile Tyr Pro Thr Pro Trp
            260                 265                 270

Tyr Asp Ile Thr Pro Lys Asn Thr Tyr Ile Pro Ile Val Asn His Trp
        275                 280                 285

Ile Asn Val Asp Lys His Ser Ser Cys
    290                 295

<210> SEQ ID NO 3
<211> LENGTH: 642
<212> TYPE: DNA
<213> ORGANISM: Staphylococcus hyicus

<400> SEQUENCE: 3
atgcaccacc accaccacca caatgattcg acaacacaaa caacgacacc actggaagtc    60
gctcaaacgt cgcagcaaga aacacataca catcaaacac ctgttacatc attacatact   120
gcaacacctg aacatgttga tgactctaaa gaagcaacac ctttacctga aaaagcagag   180
tcaccaaaaa ccgaagtgac agttcaacct tcatcgcata cacaggaagt acctgcgtta   240

-continued

```
cataaaaaaa cacagcaaca accggcgtat aaggataaaa cggtaccaga gtcaacgata      300
gcatcaaagt cggttgaatc aaataaagca acagaaaatg agatgtcacc tgttgaacat      360
catgcttcaa atgtggaaaa acgtgaagat agattggaga ctaatgagac aacaccgcca      420
tcagtggacc gtgaatttag ccataaaatc atcaataatg cgcacgtaaa tccaaaaacg      480
gatggacaaa caaacgttaa tgttgatacg aaaacgatag acaccgtttc accgaaagat      540
gacagaatag atacggcgca accgaaacaa gtcgacgctc ctaaagaaaa tacaacggca      600 caaataaat ttacatcaca agcgagcgac aaaaaaccat ac                         642
```

<210> SEQ ID NO 4
<211> LENGTH: 214
<212> TYPE: PRT
<213> ORGANISM: Staphylococcus hyicus
<220> FEATURE:
<221> NAME/KEY: MISC_FEATURE
<222> LOCATION: (2)..(7)
<223> OTHER INFORMATION: His-Tag

<400> SEQUENCE: 4

```
Met His His His His His His Asn Asp Ser Thr Thr Gln Thr Thr Thr
1               5                   10                  15

Pro Leu Glu Val Ala Gln Thr Ser Gln Gln Glu Thr His Thr His Gln
                20                  25                  30

Thr Pro Val Thr Ser Leu His Thr Ala Thr Pro Glu His Val Asp Asp
            35                  40                  45

Ser Lys Glu Ala Thr Pro Leu Pro Glu Lys Ala Glu Ser Pro Lys Thr
        50                  55                  60

Glu Val Thr Val Gln Pro Ser Ser His Thr Gln Glu Val Pro Ala Leu
65                  70                  75                  80

His Lys Lys Thr Gln Gln Gln Pro Ala Tyr Lys Asp Lys Thr Val Pro
                85                  90                  95

Glu Ser Thr Ile Ala Ser Lys Ser Val Glu Ser Asn Lys Ala Thr Glu
            100                 105                 110

Asn Glu Met Ser Pro Val Glu His His Ala Ser Asn Val Glu Lys Arg
        115                 120                 125

Glu Asp Arg Leu Glu Thr Asn Glu Thr Thr Pro Pro Ser Val Asp Arg
130                 135                 140

Glu Phe Ser His Lys Ile Ile Asn Asn Ala His Val Asn Pro Lys Thr
145                 150                 155                 160

Asp Gly Gln Thr Asn Val Asn Val Asp Thr Lys Thr Ile Asp Thr Val
                165                 170                 175

Ser Pro Lys Asp Asp Arg Ile Asp Thr Ala Gln Pro Lys Gln Val Asp
            180                 185                 190

Ala Pro Lys Glu Asn Thr Thr Ala Gln Asn Lys Phe Thr Ser Gln Ala
        195                 200                 205

Ser Asp Lys Lys Pro Tyr
210
```

<210> SEQ ID NO 5
<211> LENGTH: 50
<212> TYPE: DNA
<213> ORGANISM: Artificial sequence
<220> FEATURE:
<223> OTHER INFORMATION: Forward primer for 207 amino acid His-tagged propeptide from Staphylococcus hyicus

```
<400> SEQUENCE: 5
catatgcacc accaccacca ccacaatgat tcgacaacac aaacaacgac            50

<210> SEQ ID NO 6
<211> LENGTH: 30
<212> TYPE: DNA
<213> ORGANISM: Artificial sequence
<220> FEATURE:
<223> OTHER INFORMATION: Reverse primer for 207 amino acid His-tagged
      propeptide from Staphylococcus hyicus

<400> SEQUENCE: 6
ggatccgtat ggtttttttgt cgctcgcttg                                 30

<210> SEQ ID NO 7
<211> LENGTH: 38
<212> TYPE: DNA
<213> ORGANISM: Artificial sequence
<220> FEATURE:
<223> OTHER INFORMATION: Forward primer for cloning of codon-optimized
      gene wbgL via NcoI into pACYCDuet-1

<400> SEQUENCE: 7
gatcaccatg ggcagcatta ttcgtctgca gggtggtc                         38

<210> SEQ ID NO 8
<211> LENGTH: 43
<212> TYPE: DNA
<213> ORGANISM: Artificial sequence
<220> FEATURE:
<223> OTHER INFORMATION: Reverse primer for cloning of codon-optimized
      gene wbgL via BamHI into pACYCDuet-1

<400> SEQUENCE: 8
gatcaggatc cttagcagct gctatgttta tcaacgttga tcc                   43
```